(12) United States Patent
Kawamoto et al.

(10) Patent No.: US 6,180,621 B1
(45) Date of Patent: *Jan. 30, 2001

(54) **METHOD AND TREATMENT USING 1-METHYLCARBAPENEM DERIVATIVES AS AN ANTI-*HELICOBACTER PYLORI* AGENT**

(75) Inventors: Isao Kawamoto; Satoshi Ohya, both of Tokyo; Yukio Utsui, Tokorozawa, all of (JP)

(73) Assignee: Sankyo Company, Limited, Tokyo (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/187,680

(22) Filed: Nov. 6, 1998

Related U.S. Application Data

(63) Continuation of application No. PCT/JP97/01542, filed on May 8, 1997.

(30) Foreign Application Priority Data

May 9, 1996 (JP) .................................................... 8-114448

(51) Int. Cl.[7] .......................... A01N 43/00; A61K 31/395
(52) U.S. Cl. ........................ 514/210; 514/193; 514/202; 514/205; 514/209
(58) Field of Search .................................. 514/210, 193, 514/202, 205, 209

(56) References Cited

U.S. PATENT DOCUMENTS

| | | | |
|---|---|---|---|
| 5,153,187 | * 10/1992 | Iwasaki et al. | 514/210 |
| 5,424,306 | * 6/1995 | Kawamoto et al. | 514/210 |
| 5,607,671 | * 3/1997 | Heino | 424/94.1 |

FOREIGN PATENT DOCUMENTS

| | | |
|---|---|---|
| 642797 | 3/1995 | (EP) . |
| 7-45499 | 2/1990 | (JP) . |
| 2-223587 | 9/1990 | (JP) . |
| 4-279588 | 10/1992 | (JP) . |
| 8-53453 | 2/1996 | (JP) . |

OTHER PUBLICATIONS

G.E. Buck et al., "Relation of *Campylobacter pyloridis* to Gastritis and Peptic Ulcer", *J. Infect. Dis.*, 153, 664–669 (1986).

G. Geis et al., "Unusual Fatty Acid Substitution in Lipids and Lipopolysaccharides of *Helicobacter pylori*", *J. Clinical Microbiology*, 930–932 (1990).

* cited by examiner

Primary Examiner—Frederick Krass
(74) Attorney, Agent, or Firm—Frishauf, Holtz, Goodman, Langer & Chick, P.C.

(57) ABSTRACT

A method for the prophylaxis or treatment of infectious diseases caused by *helicobacter pyloir*, by administering a pharmacologically effective amount of a 1-methoylcarbapenem coumpund of formula (I) or a pharmacologically acceptable salt or ester thereof:

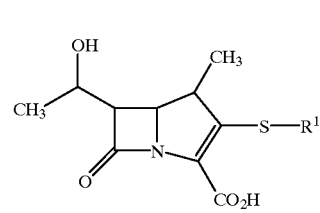

(I)

$R^1$ represents a group of the following formula:

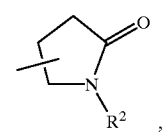

(IIa)

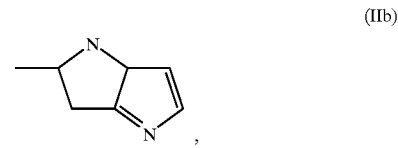

(IIb)

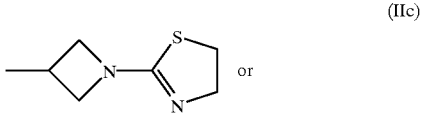

(IIc)

or

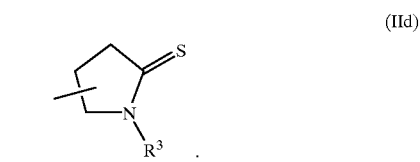

(IId)

$R^2$ is a hydrogen atom or a $C_1$–$C_6$ alkyl group, and $R^3$ is a hydrogen atom or a $C_1$–$C_6$ alkyl group.

32 Claims, 1 Drawing Sheet

Therapeutic effects for nude mice infected with *helicobacter pylori*

METHOD AND TREATMENT USING 1-METHYLCARBAPENEM DERIVATIVES AS AN ANTI-*HELICOBACTER PYLORI* AGENT

This application is a continuation application of International Application PCT/JP97/01542 filed May 8, 1997.

BACKGROUND OF THE INVENTION

1. Field of the Invention

The present invention relates to an anti-*helicobacter pylori* composition comprising 1-methylcarbapenem derivatives or pharmacologically acceptable salts or esters thereof as an active ingredient, use of the derivatives, salts or esters for the preparation of an anti-*helicobacter pylori* medicament and a method which comprises administering a pharmacologically effective amount of the derivatives, salts or esters to warm-blooded animals for treatment and prevention of infectious diseases caused by *helicobacter pylori*.

2. Background Information

According to recent studies, there are a number of reports on the phenomenon that *helicobacter pylori* is detected at a high ratio in patients suffering from chronic gastritis or digestive ulcers, and that such gastrointestinal disorders are cured by the eradication of *helicobacter pylori*; and on the phenomenon that the recurrence ratio of digestive ulcers shows a drastic decrease as a result of the eradication of this bacterium. It is therefore thought that infection with this bacterium relates to chronic and digestive ulcers and, furthermore, it even has a close relationship with gastric cancer or gastritis (G. E. Buck et al., J. Infect. Dis., 153, 664–669(1986), G. Geis et al., J. Clinical Microbiology, 930–932(1990), etc.).

At present, it is reported that bismuth compounds such as bismuth citrate, nitroimidazole compounds such as metronidazole and antibiotics such as tetracycline, amoxicillin and clarithromycin are effective against *helicobacter pylori*. None of these compounds has sufficient antibacterial activity and each has a chemical structure markedly different from that of the 1-methylcarbapenem derivatives which are an active ingredient to be employed in the present invention.

The 1-methylcarbapenem derivatives, which are an active ingredient of the present invention, are known compounds (for example, Japanese Patent Publication No. Hei 745499, Japanese Patent Application Kokai No. Hei 2-223587, Japanese Patent Application Kokai No. Hei 4-279588, Japanese Patent Application Kokai No. Hei 8-53453 etc.), but their anti-*helicobacter pylori* activity is not known at all.

SUMMARY OF THE INVENTION

The present inventors have carried out an extensive investigation into the antibacterial activity of 1-methylcarbapenem derivatives. As a result, it has been found that specific 1-methylcarbapenem derivatives have excellent anti-*helicobacter pylori* activity and are useful as an active ingredient in an anti-*helicobacter pylori* composition (treatment or prevention of infectious diseases caused by *helicobacter pylori*, particularly, treatment).

The present invention provides an anti-*helicobacter pylori* composition comprising 1-methylcarbapenem derivatives or pharmacologically acceptable salts or esters thereof as an active ingredient, use of the derivatives, salts or esters for the preparation of an anti-*helicobacter pylori* medicament and a method comprising administering a pharmacologically effective amount of the derivatives, salts or esters to warm-blooded animals for treatment and prevention of infectious diseases caused by *helicobacter pylori*.

1-Methylcarbapenem derivatives, an active ingredient of the present invention, have the following formula:

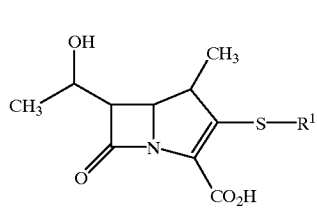

(I)

wherein $R^1$ represents a group of the following formula:

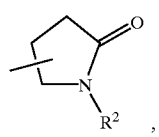

(IIa)

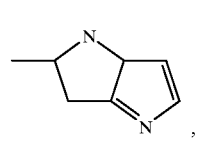

(IIb)

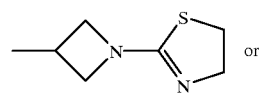 or (IIc)

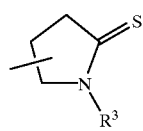

(IId)

$R^2$ represents a hydrogen atom or a $C_1$–$C_6$ alkyl group, and $R^3$ represents a hydrogen atom or a $C_1$–$C_6$ alkyl group.

DETAILED DESCRIPTION OF THE INVENTION

Figure 1:
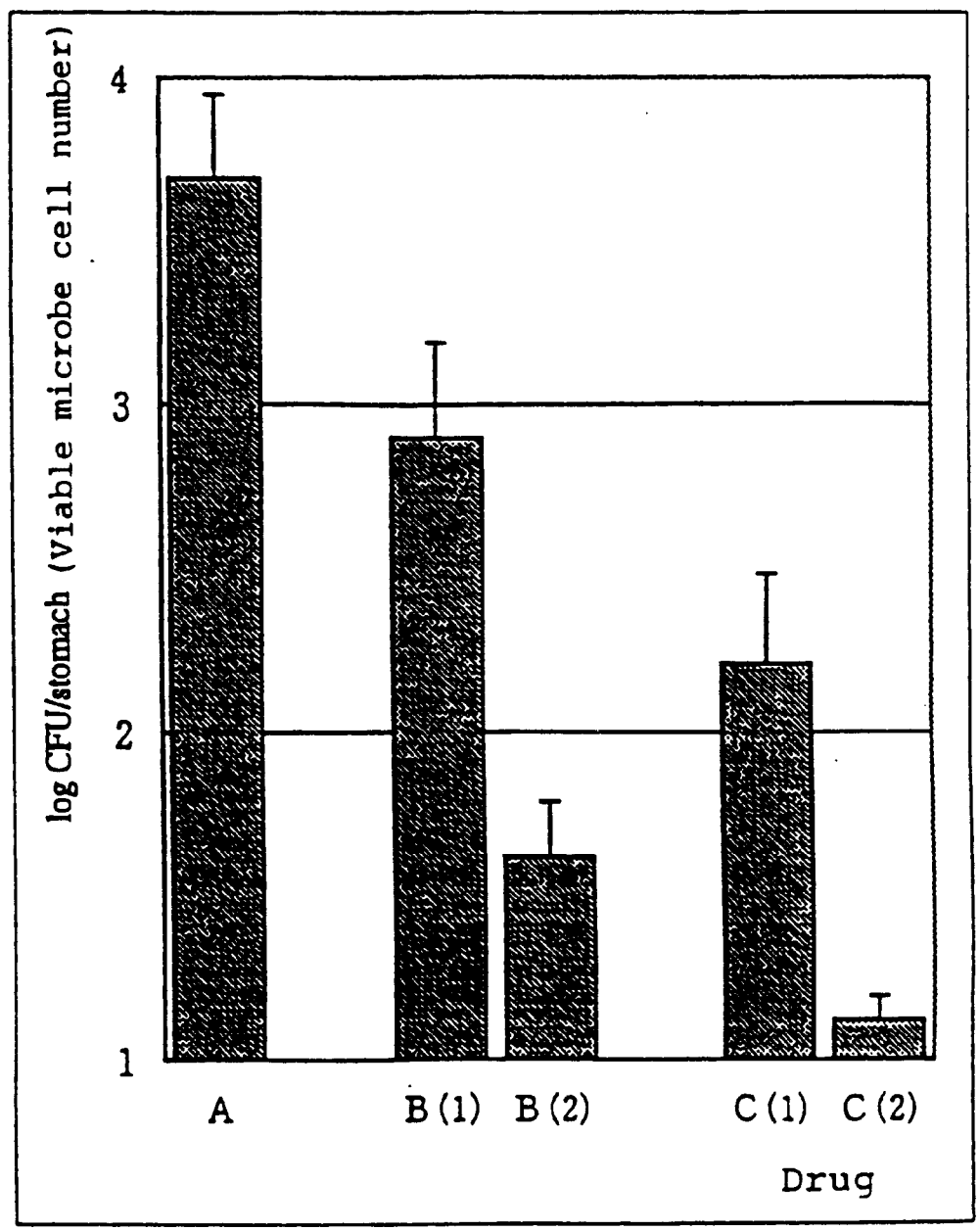
FIG. 1 is a graph depicting the effect of the treatment on mice.

In the above formula (I), examples of the $C_1$–$C_6$ alkyl group of $R^2$ or $R^3$ include methyl, ethyl, propyl, isopropyl, butyl, isobutyl, s-butyl t-butyl, pentyl and hexyl groups, preferably the $C_1$–$C_4$ alkyl groups, more preferably the methyl or ethyl group and most preferably the methyl group.

$R^1$ is preferably the group of the formula (IIa).

The oxopyrrolidinyl part of the group of the formula (la) is preferably a 2-oxo-3-pyrrolidinyl or 2-oxo-4-pyrrolidinyl group and most preferably the 2-oxo4-pyrrolidinyl group.

The thioxopyrrolidinyl part of the group of the formula (IId) is preferably a 2-thioxo-3-pyrrolidinyl or 2-thioxo-4-pyrrolidinyl group, and most preferably the 2-thioxo4-pyrrolidinyl group.

The pharmacologically acceptable salts of Compound (I) which are also an active ingredient of the present invention are salts of Compound (I) which exhibit antibacterial activity and are usable as a medicament when administered to a living body. Examples include inorganic salts such as lithium salts, sodium salts, potassium salts, calcium salts and magnesium salts; ammonium salts; and organic amine salts such as triethylamine salts, diisopropylamine salts and cyclohexylamine salts; preferably lithium salts, sodium salts and potassium salts; more preferably sodium salts and potassium salts; and most preferably sodium salts.

The pharmacologically acceptable esters of Compound (I) which are also an active ingredient of the present invention are esters of the compound (I) which exhibit antibacterial activity and are usable as a medicament when administered to a living body; and preferably esters which can be hydrolyzed in vivo and converted to the corresponding carboxylic acids. Specific examples include:

$C_1$–$C_4$ alkyl esters (preferably, methyl and ethyl esters), $C_1$–$C_4$ alkoxycarbonyloxy-($C_1$–$C_4$ alkyl) esters [for example, methoxycarbonyloxymethyl esters, 1-(methoxycarbonyloxy)ethyl esters, ethoxycarbonyloxymethyl esters, 1-(ethoxycarbonyloxy)ethyl esters, propoxycarbonyloxymethyl esters, 1-(propoxycarbonyloxy)ethyl esters, isopropoxycarbonyloxymethyl esters, 1-(isopropoxycarbonyloxy)ethyl esters, butoxycarbonyloxymethyl esters, 1-(butoxycarbonyloxy)ethyl esters, isobutoxycarbonyloxymethyl esters, 1-(isobutoxycarbonyloxy)ethyl esters, t-butoxycarbonyloxymethyl esters, 1-(t-butoxycarbonyloxy)ethyl esters, 1-(t-butoxycarboyloxy)propyl esters and 1-(t-butoxycarbonyloxy)butyl esters, of which the methoxycarbonyloxymethyl esters, 1-(methoxycarbonyloxy)ethyl esters, ethoxycarbonyloxymethyl esters, 1-(ethoxycarbonyloxy) ethyl esters, isopropoxycarbonyloxymethyl esters, 1-(isopropoxycarbonyloxy)ethyl esters, t-butoxycarbonyloxymethyl esters or 1-(t-butoxycarbonyloxy)ethyl esters are preferred, the 1-(methoxycarbonyloxy)ethyl esters, 1-(ethoxycarbonyloxy)ethyl esters, 1-(isopropoxycarbonyloxy)ethyl esters, t-butoxycarbonyloxymethyl esters and 1-(t-butoxycarbonyloxy)ethyl esters being more preferred and the 1-(isopropoxycarbonyloxy)ethyl esters being most preferred], $C_5$–$C_6$ cycloalkyloxycarbonyloxy-($C_1$–$C_4$ alkyl) esters [for example, cyclopentyloxycarbonyloxymethyl esters, 1-(cyclopentyloxycarbonyloxy)ethyl esters, cyclohexyloxycarbonyloxymethyl esters, 1-(cyclohexyloxycarbonyloxy) ethyl esters, 1-(cyclohexyloxycarbonyloxy)propyl esters and 1-(cyclohexyloxycarbonyloxy)butyl esters, of which the cyclopentyloxycarbonyloxymethyl esters, 1-(cyclopentyloxycarbonyloxy)ethyl esters, cyclohexyloxycarbonyloxymethyl esters and 1-(cyclohexyloxycarbonyloxy)ethyl esters are preferred, the 1-(cyclopentyloxycarbonyloxy)ethyl esters and 1-(cyclohexyloxycarbonyloxy)ethyl esters being more preferred, and the 1-(cyclohexyloxycarbonyloxy)ethyl esters being most preferred;

$C_2$–$C_5$ alkanoyloxy-($C_1$–$C_4$ alkyl) esters [for example, acetoxymethyl esters, 1-(acetoxy)ethyl esters, 1-(acetoxy) propyl esters, 1-(acetoxy)butyl esters, propionyloxymethyl esters, 1-(propionyloxy)ethyl esters, butyryloxymethyl esters, 1-(butyryloxy)ethyl esters, isobutyryloxymethyl esters, 1-(isobutyryloxy)ethyl esters, 1-(isobutyryloxy) propyl esters, 1-(isobutyryloxy)butyl esters, pivaloyloxymethyl esters, 1-(pivaloyloxy)ethyl esters, 1-(pivaloyloxy) propyl ester and 1-(pivaloyloxy)butyl esters, of which the acetoxymethyl esters, 1-(acetoxy)ethyl esters, propionyloxymethyl esters, 1-(propionyloxy)ethyl esters, butyryloxymethyl esters, 1-(butyryloxy)ethyl esters, isobutyryloxymethyl esters, 1-(isobutyryloxy)ethyl esters, pivaloyloxymethyl esters and 1-(pivaloyloxy)ethyl esters are preferred, the acetoxymethyl esters, 1-(acetoxy)ethyl esters, isobutyryloxymethyl esters, 1-(isobutyryloxy)ethyl esters, pivaloyloxymethyl esters and 1-(pivaloyloxy)ethyl esters being more preferred, and the pivaloyloxymethyl esters being most preferred];

($C_5$–$C_6$ cycloalkylcarbonyloxy)- or (1-alkyl-$C_5$–$C_6$ cycloalkylcarbonyloxy)-($C_1$–$C_4$ alkyl) esters [for example, cyclopentylcarbonyloxymethyl esters, 1-(cyclopentylcarbonyloxy)ethyl esters, 1-methylcyclopentylcarbonyloxymethyl esters, 1-(1-methylcyclopentylcarbonylxoy)ethyl esters, 1-ethylcyclopentylcarbonyl-oxymethyl esters, 1(1-ethylcyclopentylcarbonyloxy)ethyl esters, cyclohexylcarbonyloxymethyl esters, 1-(cyclohexylcarbonyloxy)ethyl esters, 1-(cyclohexylcarbonyloxy)propyl esters, 1-(cyclohexylcarbonyloxy)butyl esters, 1-methylcyclohexylcarbonyloxymethyl esters, 1-(1-methylcyclohexylcarbonyloxy)ethyl esters, 1-(1-methylcyclohexylcarbonyloxy)propyl esters, 1-(1-methylcyclohexylcarboyloxy)butyl esters, 1-ethylcyclohexylcarbonyloxymethyl esters, 1-(1-ethylcyclohexylcarbonyloxy)ethyl esters, 1(1-propylcyclohexylcarbonyloxymethyl esters and 1-butylcyclohexylcarbonyloxymethyl esters, of which the cyclopentylcarbonyloxymethyl esters, 1-(cyclopentylcarbonyloxy)ethyl esters, 1-methylcyclopentylcarbonyloxymethyl esters, 1-(1-methylcyclopentylcarbonyloxy)ethyl esters, 1-ethylcyclopentylcarbonyloxymethyl esters, cyclohexylcarbonyloxymethyl esters, 1-(cyclohexylcarbonyloxy)ethyl esters, 1-methylcyclohexylcarbonyloxymethyl esters, 1-(1-methylcyclohexylcarbonyloxy)ethyl esters and 1-ethylcyclohexylcarbonyloxymethyl esters are preferred, the cyclopentylcarbonyloxymethyl esters, 1-(cyclopentylcarbonyloxy)ethyl esters, 1-methylcyclopentylcarbonyloxymethyl esters, 1(1-methylcyclopentylcarbonyloxy)ethyl esters, cyclohexylcarbonyloxymethyl esters, 1-(cyclohexylcarbonyloxy)ethyl esters, 1-methylcyclohexylcarbonyloxymethyl esters and 1-(1 -methylcyclohexylcarbonyloxy)ethyl esters being more preferred, the cyclopentylcarbonyloxymethyl esters, 1-methylcyclopentylcarbonyloxymethyl esters, cyclohexylcarbonyloxymethyl esters and 1-methylcyclohexylcarbonyloxymethyl esters being much more preferred, and the 1-methylcyclohexylcarbonyloxymethyl esters being most preferred];

phthalidyl esters; and 5-($C_1$–$C_4$ alkyl- or phenyl-)-2-oxo-1,3-dioxolen 4ylmethyl esters [for example, 5-methyl-2-oxo-1,3-dioxoleno-4-ylmethyl esters, 5-ethyl-2-oxo-1,3-dioxolen-4-ylmethyl esters, 5-propyl-2-oxo-1,3-dioxolen-4-ylmethyl esters, 5-butyl-2-oxo-1,3-dioxolen-4-ylmethyl esters and 5-phenyl-2-oxo-1,3-dioxolen-4-ylmethyl esters, of which the 5-methyl-2-oxo-1,3-dioxolen4-ylmethyl esters, 5-ethyl-2-oxo-1,3-dioxolen-4-ylmethyl esters and 5-phenyl-2-oxo-1, 3-dioxolen4-ylmethyl esters are preferred, the 5-methyl-2-oxo-1,3-dioxolen-4-ylmethyl esters and 5-phenyl-2-oxo-1, 3-dioxolen-4-ylmethyl esters being more preferred, and the 5-methyl-2-oxo-1,3-dioxolen4-ylmethyl esters being most preferred].

Among these esters, the methoxycarbonyloxymethyl esters, 1-(methoxycarbonyloxy)ethyl esters, ethoxycarbonyloxymethyl esters, 1-(ethoxycarbonyloxy)ethyl esters, isopropoxycarbonyloxymethyl esters, 1-(isopropoxycarbonyloxy)ethyl esters, t-butoxycarbonyloxymethyl esters, 1-butoxycarbonyloxy) ethyl esters, cyclopentyloxycarbonyloxymethyl esters, 1-(cyclopentyloxycarbonyloxy)ethyl esters, cyclohexyloxycarbonyloxymethyl esters, 1-(cyclohexyloxycarbonyloxy) ethyl esters, acetoxymethyl esters, 1-(acetoxy)ethyl esters, propionyloxymethyl esters, 1-(propionyloxy)ethyl esters, butyryloxymethyl esters, 1-(butyryloxy)ethyl esters, isobutyryloxymethyl esters, 1-(isobutyryloxy)ethyl esters, pivaloyloxymethyl esters, 1-(pivaloyloxy)ethyl esters, cyclopentylcarbonyloxymethyl esters, 1-(cyclopentylcarbonyloxy)ethyl esters, 1-methylcyclopentylcarbonyloxymethyl esters, 1-(1-methylcyclopentylcarbonyloxy)ethyl esters, 1-ethylcyclopentylcarbonyloxymethyl esters, cyclohexylcarbonyloxymethyl esters, 1-(cyclohexylcarbonyloxy)ethyl esters, 1-methylcyclohexylcarbonyloxymethyl esters, 1-(1-methylcyclohexylcarbonyloxy)ethyl esters, 1-ethylcyclohexylcarbonyloxymethyl esters, phthalidyl esters, 5-methyl-2-oxo-1,3-dioxolen4-ylmethyl esters, 5-ethyl-2-oxo-1,3-dioxolen-4-ylmethyl esters and 5-phenyl-2-oxo-1,3-dioxolen-4-ylmethyl esters are preferred;

the 1-(methoxycarbonyloxy)ethyl esters, 1-(ethoxycarbonyloxy)ethyl esters, 1-(isopropoxycarbonyloxy)ethyl esters, t-butoxycarbonyloxymethyl esters, 1-(t-butoxycarbonyloxy) ethyl esters, 1-(cyclopentyloxycarbonyloxy)ethyl esters, 1-(cyclohexyloxycarbonyloxy)ethyl esters, acetoxymethyl esters, 1-(acetoxy)ethyl esters, isobutyryloxymethyl esters, 1-isobutyryloxy)ethyl esters, pivaloyloxymethyl esters, 1-(pivaloyloxy)ethyl esters, cyclopentylcarbonyloxymethyl esters, 1-(cyclopentylcarbonyloxy)ethyl esters, 1-methylcyclopentylcarbonyloxymethyl esters, 1-(1-methylcyclopentylcarbonyloxy)ethyl esters, cyclohexylcarbonyloxymethyl esters, 1-(cyclohexylcarbonyloxy)ethyl esters, 1-methylcyclohexylcarbonyloxymethyl esters, 1-(1-methylcyclohexylcarbonyloxy)ethyl esters, phthalidyl esters, 5-methyl-2-oxo-1,3-dioxolen4-ylmethyl esters and 5-phenyl-2-oxo-1,3-dioxolen-4-ylmethyl esters are more preferred;

the 1-(methoxycarbonyloxy)ethyl esters, 1-(ethoxycarbonyloxy)ethyl esters, 1-(isopropoxycarbonyloxy)ethyl esters, t-butoxycarbonyloxymethyl esters, 1-(t-butoxycarbonyloxy) ethyl esters, 1-(cyclopentyloxycarbonyloxy)ethyl esters, 1-(cyclohexyloxycarbonyloxy)ethyl esters, acetoxymethyl esters, 1-(acetoxy)ethyl esters, isobutyryloxymethyl esters, 1-(isobutyryloxy)ethyl esters, pivaloyloxymethyl esters, 1-(pivaloyloxy)ethyl esters, cyclopentylcarbonyloxymethyl esters, 1-methylcyclopentylcarbonyloxymethyl esters, cyclohexylcarbonyloxymethyl esters, 1-methylcyclohexylcarbonyloxymethyl esters, phthalidyl esters and 5-methyl-2-oxo-1,3-dioxolen-4-ylmethyl esters are still more preferred;

the 1-(isopropoxycarbonyloxy)ethyl esters, 1-(cyclohexyloxycarbonyloxy)ethyl esters, pivaloyloxymethyl esters, 1-methylcyclohexylcarboyloxymethyl esters and 5-methyl-2-oxo-1,3-dioxolen 4ylmethyl esters are particularly preferred; and the 1-(isopropoxycarbonyloxy)ethyl esters, 1-(cyclohexyloxycarbonyloxy)ethyl esters and pivaloyloxymethyl esters are most preferred.

Compound (I) which is an active ingredient of the present invention contains asymmetric carbons in its molecule and therefore has various isomers with respect to them. The present application embraces various isomers of Compound (I) and mixtures of these isomers, of which the isomers having a (1R,5S,6S) configuration and an R configuration for the hydroxyl group at the α-position of the 6-substituent in the carbapenem skeleton, are preferred. The present application also embraces hydrated products of Compound (I) and its salts and esters.

Preferred examples of the compounds of formula (I) include:

(1) a compound wherein $R^1$ represents a group of formula (IIa) (in which $R^2$ represents a hydrogen atom or a $C_1$–$C_4$ alkyl group), a group of formula (IIb), a group of formula (IIc) or a group of formula (IId) (in which $R^3$ represents a hydrogen atom or a methyl group), (2) a compound wherein $R^1$ represents a group of formula (IIa) (in which $R^2$ represents a hydrogen atom or a methyl group), (3) a compound wherein $R^1$ represents a 2-oxo-3-pyrrolidinyl, 1-methyl-2-oxo-3-pyrrolidinyl, 2-oxo-4-pyrrolidinyl or 1-methyl-2-oxo4-pyrrolidinyl group, (4) a compound wherein $R^1$ represents a 2-oxo4-pyrrolidinyl or 1-methyl-2-oxo-4-pyrrolidinyl group, (5) a compound wherein $R^1$ represents a 2-oxo-4pyrrolidinyl group, (6) a compound wherein the configuration in the carbapenem skeleton is a (1R,5S,6S) configuration, (7) a compound wherein the configuration of the hydroxyl group at the α-position of the 6-substituent in the carbapenem skeleton is a R configuration, (8) a compound whose pharmacologically acceptable salt is a lithium salt, sodium salt or potassium salt, (9) a compound whose pharmacologically acceptable salt is a sodium salt or potassium salt,

(10) a compound whose pharmacologically acceptable salt is a sodium salt,

(11) a compound whose pharmacologically acceptable ester can be hydrolyzed in vivo and converted into the corresponding carboxylic acid,

(12) a compound whose pharmacologically acceptable ester is a 1-(methoxycarbonyloxy)ethyl ester, 1-(ethoxycarbonyloxy)ethyl ester, 1-(isopropoxycarbonyloxy)ethyl ester, t-butoxycarbonyloxymethyl ester, 1-(t-butoxycarbonyloxy) ethyl ester, 1-(cyclopentyloxycarbonyloxy)ethyl ester, 1-(cyclohexyloxycarbonyloxy)ethyl ester, acetoxymethyl ester, 1-(acetoxy)ethyl ester, isobutyryloxymethyl ester, 1-(isobutyryloxy)ethyl ester, pivaloyloxymethyl ester, 1-(pivaloyloxy)ethyl ester, cyclopentylcarbonyloxymethyl ester, 1-(cyclopentylcarbonyloxy)ethyl ester, 1-methylcyclopentylcarbonyloxymethyl ester, 1-(1-methylcyclopentylcarbonyloxy)ethyl ester, cyclohexylcarbonyloxymethyl ester, 1-(cyclohexylcarbonyloxy)ethyl ester, 1-methylcyclohexylcarbonyloxymethyl ester, 1-(1-methylcyclohexylcarbonyloxy)ethyl ester, phthalidyl ester, 5-methyl-2-oxo-1,3-dioxolen-4-ylmethyl ester or 5-phenyl-2-oxo-1,3-dioxolen4-ylmethyl ester,

(13) a compound whose pharmacologically acceptable ester is a 1-(methoxycarbonyloxy)ethyl ester, 1-(ethoxycarbonyloxy)ethyl ester, 1-(isopropoxycarbonyloxy)ethyl ester, t-butoxycarbonyloxymethyl ester, 1-(t-butoxycarbonyloxy) ethyl ester, 1-(cyclopentyloxycarbonyloxy)ethyl ester, 1-(cyclohexyloxycarbonyloxy)ethyl ester, acetoxymethyl ester, 1-(acetoxy)ethyl ester, isobutyryloxymethyl ester, 1-(isobutyryloxy)ethyl ester, pivaloyloxymethyl ester, 1-(pivaloyloxy)ethyl ester, cyclopentylcarbonyloxymethyl ester, 1-methylcyclopentylcarbonyloxymethyl ester, cyclohexylcarbonyloxymethyl ester, 1-methylcyclohexylcarboyloxymethyl ester, phthalidyl ester or 5-methyl-2-oxo-1,3-dioxolen4-ylmethyl ester,

(14) a compound whose pharmacologically acceptable ester is a 1-(isopropoxycarbonyloxy)ethyl ester, 1-(cyclohexyloxycarbonyloxy)ethyl ester, pivaloyloxymethyl ester, 1-methylcyclohexylcarbonyloxymethyl ester or 5-methyl-2-oxo-1,3-dioxolen-4-ylmethyl ester, and

(15) a compound whose pharmacologically acceptable ester is a 1-(isopropoxycarbonyloxy)ethyl ester, 1-(cyclohexyloxycarbonyloxy)ethyl ester or pivaloyloxymethyl ester.

In each of the groups (1) to (5), (8) to (10) and (11) to (15), the larger the number is, the more preferred the compound is.

In addition, compounds obtained by selecting $R^1$ from the group (1) to (5), a configuration from (6) or (7), a salt from the group (8) to (10) and an ester from the group (11) to (15) and by using these in any combination are preferred. Examples of such compounds are as follows:

(16) a compound wherein $R^1$ represents a group of formula (IIa) (in which $R^2$ represents a hydrogen atom or a $C_1$–$C_4$ alkyl group), group of formula (IIb), group of formula (IIc) or group of formula (IId) (in which $R^3$ represents a hydrogen atom or a methyl group), the configuration in the carbapenem skeleton is a (1R,5S, 6S) configuration, the configuration of the hydroxyl group at the α-position of the 6-substituent in the carbapenem skeleton is a R configuration, the pharmacologically acceptable salt is a lithium salt, sodium salt or potassium salt, and the pharmacologically acceptable ester is one which can be hydrolyzed in vivo and converted into the corresponding carboxylic acid.

(17) a compound wherein $R^1$ represents a group of formula (IIa) (in which $R^2$ represents a hydrogen atom or a methyl group), the configuration in the carbapenem skeleton is a (1R,5S, 6S) configuration, the configuration of the hydroxyl group at the α-position of the 6-substituent in the carbapenem skeleton is a R configuration, the pharmacologically acceptable salt is a sodium salt or potassium salt, and the pharmacologically acceptable ester is a 1-(methoxycarbonyloxy)ethyl ester, 1-(ethoxycarbonyloxy) ethyl ester, 1-(isopropoxycarbonyloxy)ethyl ester, t-butoxycarbonyloxymethyl ester, 1-(t-butoxycarbonyloxy) ethyl ester, 1-(cyclopentyloxycarbonyloxy)ethyl ester, 1-(cyclohexyloxycarbonyloxy)ethyl ester, acetoxymethyl ester, 1-(acetoxy)ethyl ester, isobutyryloxymethyl ester, 1-(isobutyryloxy)ethyl ester, pivaloyloxymethyl ester, 1-(pivaloyloxy)ethyl ester, cyclopentylcarbonyloxymethyl ester, 1-(cyclopentylcarbonyloxy)ethyl ester, 1-(1-methylcyclopentylcarbonyloxy)ethyl ester, cyclohexylcarbonyloxymethyl ester, 1-(cyclohexylcarbonyloxy)ethyl ester, 1-methylcyclohexylcarbonyloxymethyl ester, 1-(1-methylcyclohexylcarbonyloxy)ethyl ester, phthalidyl ester, 5-methyl-2-oxo-1,3-dioxolen-4-ylmethyl ester or 5-phenyl-2-oxo-1,3-dioxolen-4-ylmethyl ester,

(18) a compound wherein $R^1$ represents a 2-oxo-3-pyrrolidinyl group, 1-methyl-2-oxo-3-pyrrolidinyl group, 2-oxo-4-pyrrolidinyl group or 1-methyl-2-oxo-4-pyrrolidinyl group, the configuration in the carbapenem skeleton is a (1R,5S, 6S) configuration, the configuration of the hydroxyl group at the α-position of the 6-substituent in the carbapenem skeleton is a R configuration, the pharmacologically acceptable salt is a sodium salt or potassium salt, and the pharmacologically acceptable ester is a 1-(methoxycarbonyloxy)ethyl ester, 1-(ethoxycarbonyloxy) ethyl ester, 1-(isopropoxycarbonyloxy)ethyl ester, t-butoxycarbonyloxymethyl ester, 1-(t-butoxycarbonyloxy) ethyl ester, 1-(cyclopentyloxycarbonyloxy)ethyl ester, 1-(cyclohexyloxycarbonyloxy)ethyl ester, acetoxymethyl ester, 1-acetoxy)ethyl ester, isobutyryloxymethyl ester, 1-(isobutyryloxy)ethyl ester, pivaloyloxymethyl ester, 1-(pivaloyloxy)ethyl ester, cyclopentylcarbonyloxymethyl ester, 1-methylcyclopentylcarbonyloxymethyl ester, cyclohexylcarbonyloxymethyl ester, 1-methylcyclohexylcarboyloxymethyl ester, phthalidyl ester or 5-methyl-2-oxo-1,3-dioxolen-4-ylmethyl ester,

(19) compounds wherein $R^1$ represents a 2-oxo-4-pyrrolidinyl group or 1-methyl-2-oxo-4-pyrrolidinyl group, the configuration in the carbapenem skeleton is a (1R,5S, 6S) configuration, the configuration of the hydroxyl group at the a-position of the 6-substituent in the carbapenem skeleton is a R configuration, the pharmacologically acceptable salt is a sodium salt or potassium salt, and the pharmacologically acceptable ester is a 1-isopropoxycarbonyloxy)ethyl ester, 1-(cyclohexyloxycarbonyloxy)ethyl ester, pivaloyloxymethyl ester, 1-methylcyclohexylcarbonyloxymethyl ester or 5-methyl-2-oxo-1,3-dioxolen-4-ylmethyl ester, and

(20) a compound wherein $R^1$ represents a 2-oxo-4-pyrrolidinyl group, the configuration in the carbapenem skeleton is a (1R,5S, 6S) configuration, the configuration of the hydroxyl group at the a-position of the 6-substituent in the carbapenem skeleton is R a configuration, the pharmacologically acceptable salt is a sodium salt, and the pharmacologically acceptable ester is a 1-(isopropoxycarbonyloxy)ethyl ester, 1-(cyclohexyloxycarbonyloxy)ethyl ester or pivaloyloxymethyl ester.

Specific examples of the compounds represented by the formula (I) can be exemplified in Table 1.

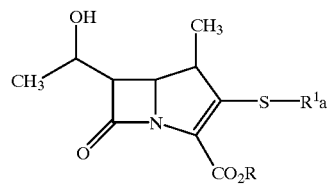

-continued

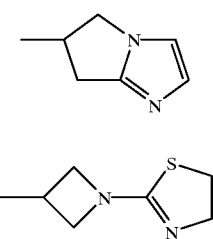
(IIb)

(IIc)

TABLE 1

| Compound No. | R | R¹a |
|---|---|---|
| 1 | H | 2-oxo-4-Pyrr |
| 2 | Na | 2-oxo-4-Pyrr |
| 3 | K | 2-oxo-4-Pyrr |
| 4 | MeOCO$_2$CHMe | 2-oxo-4-Pyrr |
| 5 | EtOCO$_2$CHMe | 2-oxo-4-Pyrr |
| 6 | Pr$^i$OCO$_2$CHMe | 2-oxo-4-Pyrr |
| 7 | Bu$^t$OCO$_2$CH$_2$ | 2-oxo-4-Pyrr |
| 8 | Bu$^t$OCO$_2$CHMe | 2-oxo-4-Pyrr |
| 9 | Pn$^c$OCO$_2$CHMe | 2-oxo-4-Pyrr |
| 10 | Hx$^c$OCO$_2$CHMe | 2-oxo-4-Pyrr |
| 11 | AcOCH$_2$ | 2-oxo-4-Pyrr |
| 12 | AcOCHMe | 2-oxo-4-Pyrr |
| 13 | Pr$^i$CO$_2$CH$_2$ | 2-oxo-4-Pyrr |
| 14 | Bu$^t$CO$_2$CH$_2$ | 2-oxo-4-Pyrr |
| 15 | Pn$^c$CO$_2$CH$_2$ | 2-oxo-4-Pyrr |
| 16 | 1-MePn$^c$CO$_2$CH$_2$ | 2-oxo-4-Pyrr |
| 17 | Hx$^c$CO$_2$CH$_2$ | 2-oxo-4-Pyrr |
| 18 | 1-MeHxCOCH$_2$ | 2-oxo-4-Pyrr |
| 19 | Phthz | 2-oxo-4-Pyrr |
| 20 | MODM | 2-oxo-4-Pyrr |
| 21 | H | 1-Me-2-oxo-4-Pyrr |
| 22 | Na | 1-Me-2-oxo-4-Pyrr |
| 23 | K | 1-Me-2-oxo-4-Pyrr |
| 24 | MeOCO$_2$CHMe | 1-Me-2-oxo-4-Pyrr |
| 25 | EtOCO$_2$CHMe | 1-Me-2-oxo-4-Pyrr |
| 26 | Pr$^i$OCO$_2$CHMe | 1-Me-2-oxo-4-Pyrr |
| 27 | Bu$^t$OCO$_2$CH$_2$ | 1-Me-2-oxo-4-Pyrr |
| 28 | Bu$^t$OCO$_2$CHMe | 1-Me-2-oxo-4-Pyrr |
| 29 | Pn$^c$OCO$_2$CHMe | 1-Me-2-oxo-4-Pyrr |
| 30 | Hx$^c$OCO$_2$CHMe | 1-Me-2-oxo-4-Pyrr |
| 31 | AcOCH$_2$ | 1-Me-2-oxo-4-Pyrr |
| 32 | AcOCHMe | 1-Me-2-oxo-4-Pyrr |
| 33 | Pr$^i$OCO$_2$CH$_2$ | 1-Me-2-oxo-4-Pyrr |
| 34 | Bu$^t$CO$_2$CH$_2$ | 1-Me-2-oxo-4-Pyrr |
| 35 | Pn$^c$CO$_2$CH$_2$ | 1-Me-2-oxo-4-Pyrr |
| 36 | 1-MePn$^c$CO$_2$CH$_2$ | 1-Me-2-oxo-4-Pyrr |
| 37 | Hx$^c$CO$_2$CH$_2$ | 1-Me-2-oxo-4-Pyrr |
| 38 | 1-MeHx$^c$CO$_2$CH$_2$ | 1-Me-2-oxo-4-Pyrr |
| 39 | Phthz | 1-Me-2-oxo-4-Pyrr |
| 40 | MODM | 1-Me-2-oxo-4-Pyrr |
| 41 | H | 2-oxo-3-Pyrr |
| 42 | Na | 2-oxo-3-Pyrr |
| 43 | K | 2-oxo-3-Pyrr |
| 44 | MeOCO$_2$CHMe | 2-oxo-3-Pyrr |
| 45 | EtOCO$_2$CHMe | 2-oxo-3-Pyrr |
| 46 | Pr$^i$OCO$_2$CHMe | 2-oxo-3-Pyrr |
| 47 | Bu$^t$OCO$_2$CH$_2$ | 2-oxo-3-Pyrr |
| 48 | Bu$^t$CO$_2$CHMe | 2-oxo-3-Pyrr |
| 49 | AcOCH$_2$ | 2-oxo-3-Pyrr |
| 50 | AcOCHMe | 2-oxo-3-Pyrr |
| 51 | Pr$^i$CO$_2$CH$_2$ | 2-oxo-3-Pyrr |
| 52 | Bu$^t$CO$_2$CH$_2$ | 2-oxo-3-Pyrr |
| 53 | 1-MePn$^c$CO$_2$CH$_2$ | 2-oxo-3-Pyrr |
| 54 | 1-MeHx$^c$CO$_2$CH$_2$ | 2-oxo-3-Pyrr |
| 55 | Phthz | 2-oxo-3-Pyrr |
| 56 | MODM | 2-oxo-3-Pyrr |
| 57 | H | 1-Me-2-oxo-3-Pyrr |
| 58 | Na | 1-Me-2-oxo-3-Pyrr |
| 59 | K | 1-Me-2-oxo-3-Pyrr |
| 60 | MeOCO$_2$CHMe | 1-Me-2-oxo-3-Pyrr |
| 61 | Pr$^i$OCO$_2$CHMe | 1-Me-2-oxo-3-Pyrr |

TABLE 1-continued

| Compound No. | R | R¹a |
|---|---|---|
| 62 | Bu$^t$OCO$_2$CH$_2$ | 1-Me-2-oxo-3-Pyrr |
| 63 | Bu$^t$OCO$_2$CHMe | 1-Me-2-oxo-3-Pyrr |
| 64 | AcOCH$_2$ | 1-Me-2-oxo-3-Pyrr |
| 65 | AcOCHMe | 1-Me-2-oxo-3-Pyrr |
| 66 | Pr$^i$CO$_2$CH$_2$ | 1-Me-2-oxo-3-Pyrr |
| 67 | Bu$^t$CO$_2$CH$_2$ | 1-Me-2-oxo-3-Pyrr |
| 68 | 1-MePn$^c$CO$_2$CH$_2$ | 1-Me-2-oxo-3-Pyrr |
| 69 | 1-MeHx$^c$CO$_2$CH$_2$ | 1-Me-2-oxo-3-Pyrr |
| 70 | Phthz | 1-Me-2-oxo-3-Pyrr |
| 71 | MODM | 1-Me-2-oxo-3-Pyrr |
| 72 | H | ImdzoPyrr |
| 73 | Na | ImdzoPyrr |
| 74 | K | ImdzoPyrr |
| 75 | Pr$^i$OCO$_2$CHMe | ImdzoPyrr |
| 76 | Bu$^t$CO$_2$CH$_2$ | ImdzoPyrr |
| 77 | Hx$^c$CO$_2$CHMe | ImdzoPyrr |
| 78 | H | ThizAze |
| 79 | Na | ThizAze |
| 80 | K | ThizAze |
| 81 | Pr$^i$OCO$_2$CHMe | ThizAze |
| 82 | Bu$^t$CO$_2$CH$_2$ | ThizAze |
| 83 | Hx$^c$CO$_2$CHMe | ThizAze |
| 84 | H | 2-thioxo-4-Pyrr |
| 85 | Na | 2-thioxo-4-Pyrr |
| 86 | K | 2-thioxo-4-Pyrr |
| 87 | Pr$^i$OCO$_2$CHMe | 2-thioxo-4-Pyrr |
| 88 | Bu$^t$CO$_2$CH$_2$ | 2-thioxo-4-Pyrr |
| 89 | Hx$^c$CO$_2$CHMe | 2-thioxo-4-Pyrr |
| 90 | H | 1-Me-2-thioxo-4-Pyrr |
| 91 | Na | 1-Me-2-thioxo-4-Pyrr |
| 92 | K | 1-Me-2-thioxo-4-Pyrr |
| 93 | Pr$^i$OCO$_2$CHMe | 1-Me-2-thioxo-4-Pyrr |
| 94 | Bu$^t$CO$_2$CH$_2$ | 1-Me-2-thioxo-4-Pyrr |
| 95 | Hx$^c$CO$_2$CHMe | 1-Me-2-thioxo-4-Pyrr |

In the above Table, abbreviations represent the following groups, respectively.

Ac: acetyl
Bu$^t$: t-butyl
Et: ethyl
Hx$^c$: cyclohexyl
ImdzoPyrr: group of the formula (IIb)
Me: methyl
MODM: 5-methyl-2-oxo-1,3-dioxolen-4-ylmethyl
Phthz: phthalidyl
Pn$^c$: cyclopentyl
Pn$^e$: isopropyl
Pyrr: pyrrolidinyl
ThizAze: group of the formula (Ic)

In the above table, the following compounds are preferred: Compounds Nos. 2, 3, 5, 6, 7, 8, 9, 10, 11, 12, 14, 15, 16, 17, 18, 20, 22, 23, 25, 26, 27, 28, 29, 30, 31, 32, 34, 35, 36, 37, 38, 40, 73, 76, 79, 82, 83, 85, 88, 91 and 94;

the following compounds are more preferrred: Compounds Nos. 2, 6, 10, 14, 18, 22, 26, 30, 34 and 38; and the following compounds are much more preferred:

Compound No. 2: sodium 2-(2-oxo-4-pyrrolidinylthio)-6-(1-hydroxyethyl)-1-methyl-1-carbapen-2-em-3-carboxylate, Compound No. 14: pivaloyloxymethyl 2-(2-oxo-4-pyrrolidinylthio)-6-(1-hydroxyethyl)-1-methyl-1-carbapen-2-em-3-carboxylate, Compound No. 18: 1-methylcyclohexylcarbonyloxymethyl 2-(2-oxo4-pyrrolidinylthio)-6-(1-hydroxyethyl)-1-methyl-1-carbapen-2-em-3-carboxylate, Compound No. 22: sodium 2-(1-methyl-2-oxo-4pyrrolidinylthio)-6-(1-hydroxyethyl)-1-methyl-1-carbapen-2-em-3-carboxylate, and Compound No. 34: pivaloyloxymethyl 2-(1-methyl-2-oxo4-pyrrolidinylthio)-6-(1-hydroxyethyl)-1-methyl-1-carbapen-2-em-3-carboxylate.

On the other hand, the following compounds are most preferred:

(1R,5 S,6S)-2-[(4R-2-oxo-4-pyrrolidinylthio]-6-[(1R)-1-hydroxyethyl]-1-methyl-1-carbapen-2-em-3-carboxylic acid, or the sodium salt or pivaloyloxymethyl ester thereof;

(1R,5 S,6S)-2-[(4S)-2-oxo-4-pyrrolidinylthio]-6-[(1R)-1-hydroxyethyl]-1-methyl-1-carbapen-2-em-3-carboxylic acid, or the sodium salt or pivaloyloxymethyl ester thereof;

(1R,5S,6S)-2-[(4R)-1-methyl-2-oxo-4-pyrrolidinylthio]-6-[(1R)-1-hydroxyethyl]-1-methyl- 1-carbapen-2-em-3-carboxylic acid, or sodium salt or pivaloyloxymethyl ester thereof; and (1R,5S,6S)-2-[(4S)-1-methyl-2--oxo-4-pyrrolidinylthio]-6-[(1R)-1-hydroxyethyl]-1-methyl-1-carbapen-2-em-3-carboxylic acid, or sodium salt or pivaloyloxymethyl ester thereof.

Compounds (I), each of which is an active ingredient of the present invention, are known or can be prepared easily by a known method (for example Japanese Patent Application Kokai No. Hei 7-165759, Japanese Patent Application Kokai No. Hei 2-223587, Japanese Patent Application Kokai No. Hei 8-53453, Japanese Patent Application Kokai No. Hei 4-279588, etc.).

The 1-methylcarbapenem derivatives of formula (I), active ingredients of the present invention, have excellent anti-bacterial activity against various *helicobacter pylori* and lower toxicity, and so they are useful as an anti-bacterial agent for the treatment or prevention (particularly, treatment) of infectious diseases caused by *helicobacter pylori*.

When the Compound (I) is used as an anti-bacterial agent, Compound (I) by itself or a mixture with a pharmacologically acceptable excipient, diluent, etc., can be administered orally in the form of tablets, capsules, granules, powders or syrups or parenterally in the form of injections. Of these, oral administration is recommended.

The above formulations can be prepared in a known manner by using additives. Examples of the additives include an excipient (for example sugar derivatives such as lactose, sucrose, dextrose, mannitol and sorbitol; starch derivatives such as corn starch, potato starch, α-starch, dextrin and carboxymethyl starch; cellulose derivatives such as crystalline cellulose, low-substituted hydroxypropyl cellulose, hydroxypropylmethyl cellulose, carboxymethyl cellulose, carboxymethyl cellulose calcium and internally-crosslinked carboxymethyl cellulose sodium; gum arabic; dextran; pullulan; silicate derivatives such as soft silicic acid anhydride, synthetic aluminum silicate and magnesium aluminate metasilicate; phosphate derivatives such as calcium phosphate; carbonate derivatives such as calcium carbonate; and sulfate derivatives such as calcium sulfate), a binder (for example the above-exemplified excipients, gelatin, polyvinyl pyrrolidone and Macrogol), a disintegrator (for example the above-exemplified excipients, chemically-modified starch or cellulose derivatives such as croscarmellose sodium, carboxymethyl starch sodium and crosslinked polyvinyl pyrrolidone), a lubricant (for example talc, stearic acid, metal salts of stearic acid such as calcium stearate and magnesium stearate; colloidal silica; waxes such as veegum and spermaceti; boric acid; glycol; carboxylic acids such as fumaric acid and adipic acid; sodium carboxylates such as sodium benzoate; sulfates such as sodium sulfate; leucine; lauryl sulfates such as sodium lauryl sulfate and magnesium lauryl sulfate; silicic acids such as silicic acid anhydride and silicic acid hydrate; and the same starch derivatives as those exemplified for the excipient), a stabilizer (for example paraoxybenzoates such as methyl paraben and propyl paraben; alcohols such as chlorobutanol benzyl alcohol and phenylethyl alcohol; benzalkonium chloride; phenol derivatives such as phenol and cresol; thimerosal; acetic anhydride; and sorbic acid), a corrigent (for example, ordinarily-employed sweeteners, acidifiers and flavors), a diluent and a solution-forming agent for injections (for example, water, ethanol and glycerin). The dose of Compound (I) will vary depending upon the condition and age of the patient and the like. Orally, it is administered in an amount of 30 mg (preferably 50 mg) in a single dose as a lower limit and 5000 mg (preferably 300 mg) in a single dose as an upper limit, and intravenously, it is administered in an amount of 10 mg (preferably 30 mg) in a single dose as a lower limit and 3000 mg (preferably 200 mg) in a single dose as an upper limit. It is desirable to be administered one to six times per day depending upon the conditions of the patient, i.e., the person being treated.

The anti-*helicobacter pylori* agent which contains Compound (I) of the present invention as an active ingredient may contain one or more other medicaments in addition. Any medicament that does not have adverse effects on Compound (I) of the present invention can be used. Examples include bismuth preparations (such as bismuth citrate and bismuth salicylate), nitroimidazole compounds (such as metronidazole), $H_2$ blocker type anti-ulcereratives (such as cimetidine, ranitidine hydrochloride, famotidine, roxatidine acetate hydrochloride and nizatidine), proton-pump inhibitor type anti-ulceratives (such as omeprazole, lansoprazole, rabeprazole, reminoprazole and saviprazole), mucous membrane protective factor enhancer type anti-ulceratives (such as plaunotol, teprenone and sofalcone), anti-bacterials (such as clarithromycin, azithromycin, erythromycin, roxithromycin and amoxicillin) and synthetic anti-bacterials (such as ofloxacin, levofloxacin, ciprofloxacin); preferably the bismuth preparations, nitroimidazole compounds, $H_2$ blocker type anti-ulceratives, proton-pump anti-ulceratives and mucous membrane protective factor enhancer type anti-ulceratives; more preferably, cimetidine, ranitidine hydrochloride, famotidine, roxatidine acetate hydrochloride, nizatidine, omeprazole, lansoprazole, rabeprazole, reminoprazole and saviprazole; and most preferably cimetidine, ranitidine hydrochloride, famotidine, omeprazole and lansoprazole.

The present invention will hereinafter be described more specifically by tests and preparation examples. It should, however, be understood that the present invention is not limited by these examples.

(Test 1)

In vitro activity against helicobacter pylon (MIC; $\mu$g/ml)

*Helicobacter pylori* (*H. pylori*) from storage was smeared on a 7%-equine-defibrinated-blood-added brain heart infusion agar (BHIA) plate and cultured at 37° C. for 72 hours under microaerophilic and wet conditions. The colonies thus grown were picked and suspended in physiological saline to prepare a culture solution of $10^8$ CFU/ml (viable microbe cell number per ml). The resulting culture solution was diluted to 10 to 50-fold with physiological saline, and one spot (about 10 $\mu$l) of the solution was inoculated on each of medicament-containing and medicament-free BHIA plates. Each of the plates was cultured at 37° C. for 72 hours under microaerophilic and wet conditions and the minimum inhibitory concentration (MIC: $\mu$g/ml) at which the growth of the colonies was inhibited was measured. The results are shown in Table 2.

TABLE 2

| | In vitro antibacterial activity (minimum inhibitory concentration, MIC: µg/ml) | | | | |
|---|---|---|---|---|---|
| No. of | MIC (µg/ml) | | | | |
| helicobacter pylori strain | Compound No. 1 | Compound No. 2 | Compound No. 3 | AMPC | CAM |
| 9470 | ≦0.006 | ≦0.0006 | ≦0.006 | 0.012 | 0.006 |
| 9472 | ≦0.006 | ≦0.006 | ≦0.006 | 0.025 | 0.006 |
| 9474 | ≦0.006 | — | — | 0.05 | 0.025 |
| 9824 | ≦0.006 | ≦0.006 | ≦0.006 | 0.39 | 1.5 |
| 9828 | ≦0.006 | ≦0.006 | ≦0.006 | 0.20 | 6.25 |

In the above Table 2, Compound 1 is sodium (1R,5S,6S)-2-[(4R)-2-oxo-4pyrrolidinylthio]-6-[(1R)-1-hydroxyethyl]-1-methyl-1-carbapen-2-em-3-carboxylate, Compound 2 is sodium (1R,5S,6S)-2-[(4R)-1-methyl-2-oxo-4-pyrrolidinylthio]-6[(1R)-1-hydroxyethyl]-1-methyl-1-carbapen-2-em-3-carboxylate, Compound 3 is sodium (1R,5S,6S)-2-[(4S)-1-methyl-2-oxo-4-pyrrolidinylthio]-6-[(1R)-1-hydroxyethyl]-1-methyl-1-carbapen-2-em-3-carboxylate, AMPC stands for amoxicillin and CAM stands for clarithromycin.

(Test 2)

Therapeutic effects for nude mouse infected with helicobacter pylon

Bacteria (*helicobacter pylori* 9470 strain) used for the test, which were cultured for 48 hours in a 2%-fetal-calf-serum-added brucella broth, were centrifuged. After removal of the supernatant, the residue was re-suspended in a 1/10 amount of a brucella broth. The resulting suspended solution was orally administered to each of three to five nude mice in an amount of 1.5 ml per mouse. 10 days after the infection, administration of a medicament was started. A 0.5% tragacanth suspension of a medicament was orally administered for 4 days through an oral catheter at a dose of 0.3 ml/mouse, once a day. On the day after the final administration, the stomach was extirpated, homogenized and then diluted. The viable microbe cell number (CFU/stomach) was measured and the results are shown in FIG. 1.

In FIG. 1, Medicament A is a control group, Medicaments B(1) and B(2) are CAM (clarithromycin: 1 mg/kg) and CAM (10 mg/kg), respectively, and Medicaments C(1) and C(2) are Compound 4, that is, pivaloyloxymethyl (1R,5S,6S)-2-[(4R)-2-oxo-4-pyrrolidinylthio]-6-[(1R)-1-hydroxyethyl]-1-methyl-1-carbapen-2-em-3-carboxylate (1 mg/kg) and Compound 4 (10 mg/kg), respectively. The significant difference of Medicament B(2), Medicament C(1) or C(2) is p<0.01 (vs the control group).

(Preparation Example 1)

| Capsules | |
|---|---|
| Compound 4 | 50.0 mg |
| Lactose | 128.7 |
| Corn starch | 70.0 |
| Magnesium stearate | 1.3 |
| | 250 mg |

The above-described ingredients in powdery form were mixed, shifted through a 60-mesh sieve and used to fill a 250-mg No.3 gelatin capsule to give a capsule.

We claim:

1. A method for the prophylaxis or treatment of an infectious disease caused by *helicobacter pylori,* which method comprises administering to a mammal suffering from or susceptible to such a disease a pharmacologically effective amount of an anti-*helicobacter pylori* agent, wherein said anti-*helicobacter pylori* agent is a 1-methylcarbapenem compound of formula (I), or a pharmacologically acceptable salt or ester thereof:

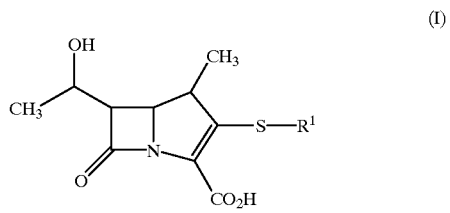

(I)

wherein:

$R^1$ represents a group of the following formula:

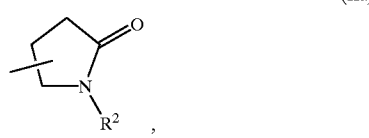

(IIa)

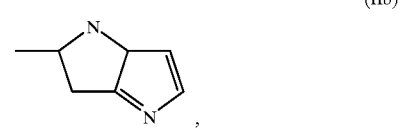

(IIb)

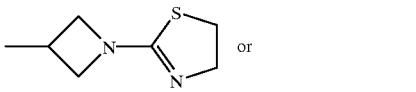 or (IIc)

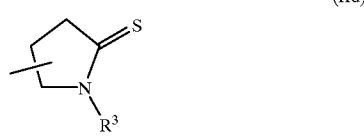

(IId)

$R^2$ represents a hydrogen atom or a $C_1$–$C_6$ alkyl group, and $R^3$ represents a hydrogen atom or a $C_1$–$C_6$ alkyl group.

2. The method of treatment according to claim 1, wherein said mammal is a human.

3. The method according to claim 2, wherein $R^1$ is a group of formula (IIa), in which $R^2$ represents a hydrogen atom or a $C_1$–$C_4$ alkyl group, a group of formula (IIb), a group of formula (IIc) or a group of formula (IId), in which $R^3$ represents a hydrogen atom or a methyl group.

4. The method according to claim 2, wherein $R^1$ is a group of formula (IIa), in which $R^2$ represents a hydrogen atom or a methyl group.

5. The method according to claim 2 wherein $R^1$ is a 2-oxo-3-pyrrolidinyl, 1-methyl-2-oxo-3-pyrrolidinyl, 2-oxo4-pyrolidinyl or 1-methyl-2-oxo-4-pyrrolidinyl group.

6. The method according to claim 2, wherein $R^1$ is a 2-oxo-4-pyrolidinyl or 1-methyl-2-oxo-4-pyrrolidinyl group.

7. The method according to claim 2, wherein $R^1$ is a 2-oxo-4-pyrolidinyl group.

8. The method according to claim 2, wherein the configuration in the carbapenem skeleton is a (1R,5S,6S) configuration.

9. The method according to claim 2, wherein the configuration of the hydroxyl group at the α-position of the 6-substituent in the carbapenem skeleton is a R configuration.

10. The method according to claim 2, wherein said agent is a salt of said compound of formula (I) selected from the group consisting of lithium salts, sodium salts and potassium salts.

11. The method according to claim 2, wherein said agent is a salt of said compound of formula (I) selected from the group consisting of sodium salts and potassium salts.

12. The method according to claim 2, wherein said agent is a sodium salt of said compound of formula (I).

13. The method according to claim 2, wherein said agent is a pharmacologically acceptable ester of said compound of formula (I) which can be hydrolyzed in vivo and converted into the corresponding carboxylic acid.

14. The method according to claim 2, in which said agent is a pharmacologically acceptable ester of said compound of formula (I) selected from the group consisting of 1-(methoxycarbonyloxy)ethyl esters, 1-(ethoxycarbonyloxy)ethyl esters, 1-(isopropoxycarbonyloxy)ethyl esters, t-butoxycarbonyloxymethyl esters, 1-(t-butoxycarbonyloxy) ethyl esters, 1-(cyclopentyloxycarbonyloxy)ethyl esters, 1-(cyclohexyloxycarbonyloxy)ethyl esters, acetoxymethyl esters, 1-(acetoxy)ethyl esters, isobutyryloxymethyl esters, 1-(isobutyryloxy)ethyl esters, pivaloyloxymethyl esters, 1-(pivaloyloxy)ethyl esters, cyclopentylcarbonyloxymethyl esters, 1-(cyclopentylcarbonyloxy)ethyl esters, 1-methylcyclopentylcarbonyloxymethyl esters, 1-(1-methylcyclopentylcarbonyloxy)ethyl esters, cyclohexylcarbonyloxymethyl esters, 1-(cyclohexylcarbonyloxy)ethyl esters, 1-methylcyclohexylcarbonyloxymethyl esters, 1-(1-methylcyclohexyl-carbonyloxy)ethyl esters, phthalidyl esters, 5-methyl-2-oxo-1,3-dioxolen-4-ylmethyl ester and 5-phenyl-2-oxo-1,3-dioxolen-4-ylmethyl esters.

15. The method according to claim 14, in which said pharmacologically acceptable ester of said compound of formula (I) is selected from the group consisting of 1-(methoxycarbonyloxy)ethyl esters, 1-(ethoxycarbonyloxy)ethyl esters, 1-(isopropoxycarbonyloxy)ethyl esters, t-butoxycarbonyloxymethyl esters, 1-(t-butoxycarbonyloxy) ethyl esters, 1-(cyclopentyloxycarbonyloxy)ethyl esters, 1-(cyclohexyloxycarbonyloxy)ethyl esters, acetoxymethyl esters, 1-(acetoxy)ethyl esters, isobutyryloxymethyl esters, 1-(isobutyryloxy)ethyl esters, pivaloyloxymethyl esters, 1-(pivaloyloxy)ethyl esters, cyclopentylcarbonyloxymethyl esters, 1-methylcyclopentylcarbonyloxymethyl esters, cyclohexylcarbonyloxymethyl esters, 1-methylcyclohexylcarbonyloxymethyl esters, phthalidyl esters and 5-methyl-2-oxo-1,3-dioxolen4-ylmethyl esters.

16. The method according to claim 14, in which said pharmacologically acceptable ester of said compound of formula (I) is selected from the group consisting of 1-(isopropoxycarbonyloxy)ethyl esters, 1-(cyclohexyloxycarbonyloxy)ethyl esters, pivaloyloxymethyl esters, 1-methylcyclohexylcarbonyloxymethyl esters and 5-methyl-2-oxo-1,3-dioxolen-4-ylmethyl esters.

17. The method according to claim 14, in which said pharmacologically acceptable ester of said compound of formula (I) is selected from the group consisting of 1-(isopropoxycarbonyloxy)ethyl esters, 1-(cyclohexyloxycarbonyloxy)ethyl esters and pivaloyloxymethyl esters.

18. The method according to claim 2, in which said agent is selected from the group consisting of:

sodium 2-(2-oxo-4-pyrrolidinylthio)-6-(1-hydroxyethyl)-1-methyl-1-carbapen-2-em-3-carboxylate, pivaloyloxymethyl 2-(2-oxo4-pyrrolidinylthio)-6-(1-hydroxyethyl)-1-methyl-1-carbapen-2-em-3-carboxylate, 1-methylcyclohexylcarbonyloxymethyl 2-(2-oxo-4-pyrrolidinylthio)-6-(1-hydroxyethyl)-1-methyl-1-carbapen-2-em-3-carboxylate, sodium 2-(1-methyl-2-oxo4-pyrrolidinylthio)-6-1-hydroxyethyl)-1-methyl-1-carbapen-2-em-3-carboxylate, and pivaloyloxymethyl 2-(1-methyl-2-oxo-4-pyrrolidinylthio)-6-(1-hydroxyethyl)-1-methyl-1-carbapen-2-em-3-carboxylate.

19. The method according to claim 18, wherein in said agent, the configuration of the carbapenem skeleton is a (1R,5S,6S) configuration and the configuration of the hydroxyl group at the a-position of the 6-substituent in the carbapenem skeleton is a R configuration.

20. The method according to claim 2, wherein said agent is (1R,5 S,6S)-2-[(4R-2-oxo-4-pyrrolidinylthio)-6-[(1R)-1-hydroxyethyl]-1-methyl-1-carbapen-2-em-3-carboxylic acid, or the sodium salt or pivaloyloxymethyl ester thereof.

21. The method according to claim 2, wherein said agent is (1R,5S,6S)-2-[(4S)-2-oxo-4-pyrrolidinylthio)-6-[(1R)-1-hydroxyethyl]-1-methyl-1-carbapen-2-em-3-carboxylic acid, or the sodium salt or pivaloyloxymethyl ester thereof.

22. The method according to claim 2, wherein said agent is (1R,5S,6S)-2-[(4R)-1-methyl-2-oxo-4-pyrrolidinylthio]-6-[(1R)-1-hydroxyethyl]-1-methyl-1-carbapen-2-em-3-carboxylic acid, or sodium salt or pivaloyloxymethyl ester thereof.

23. The method according to claim 2, wherein said agent is (1R,5S,6S)-2-[(4S)-1-methyl-2-oxo-4-pyrrolidinylthio]-6-[(1R)-1-hydroxyethyl]-1-methyl-1-carbapen-2-em-3-carboxylic acid, or sodium salt or pivaloyloxymethyl ester thereof.

24. The method according to claim 20, wherein said agent is said sodium salt.

25. The method according to claim 20, wherein said agent is said pivaloyloxymethyl ester.

26. The method according to claim 21, wherein said agent is said sodium salt.

27. The method according to claim 21, wherein said agent is said pivaloyloxymethyl ester.

28. The method according to claim 22, wherein said agent is said sodium salt.

29. The method according to claim 22, wherein said agent is said pivaloyloxymethyl ester.

30. The method according to claim 23, wherein said agent is said sodium salt.

31. The method according to claim 23, wherein said agent is said pivaloyloxymethyl ester.

32. The method according to claim 1, wherein the method is for the treatment of an infectious disease caused by *helicobacter pylori*.

* * * * *

UNITED STATES PATENT AND TRADEMARK OFFICE
CERTIFICATE OF CORRECTION

PATENT NO.   : 6,180,621 B1
DATED        : January 30, 2001
INVENTOR(S)  : Isao Kawamoto et al.

It is certified that error appears in the above-identified patent and that said Letters Patent is hereby corrected as shown below:

Title page,
ABSTRACT, replace " 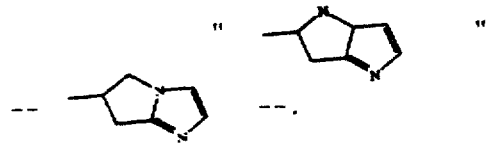 "

with  -- -- .

Column 2,
Line 25, replace " 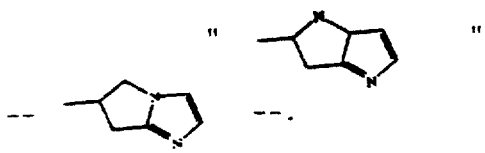 "

with  -- -- .

Line 57, replace "la" with -- IIa --.
Line 58, replace "2-oxo-4-pyrolidinyl" with -- 2-oxo-4-pyrrolidinyl --.

Column 3,
Line 28, replace "1-(t-butoxycarboyloxy) propyl" with -- 1-(t-butoxycarbonyloxy) propyl --.
Line 65, replace "propyl ester" with -- propyl esters --.

Column 4,
Line 14, replace "methylcyclopentylcarbonylxoy)ethyl" with
-- methylcyclopentylcarbonyloxy)ethyl --.
Line 23, replace "methylcyclohexycarboyloxy)butyl" with
-- methylcyclohexycarbonyloxy)butyl --.

Column 5,
Line 59, replace "1-methylcyclohexylcarboyloxymethyl" with
-- 1-methylcyclohexylcarbonyloxymethyl --.

Column 7,
Line 4, replace "1-methylcyclohexylcarboyloxymethyl" with
-- 1-methylcyclohexylcarbonyloxymethyl --.

Column 8,
Line 24, replace "1-methylcyclohexylcarboyloxymethyl" with
-- 1-methylcyclohexylcarbonyloxymethyl --.

UNITED STATES PATENT AND TRADEMARK OFFICE
CERTIFICATE OF CORRECTION

PATENT NO. : 6,180,621 B1
DATED : January 30, 2001
INVENTOR(S) : Isao Kawamoto et al.

It is certified that error appears in the above-identified patent and that said Letters Patent is hereby corrected as shown below:

Column 9,
Line 1, before "(IIb)", insert the following:
-- wherein $R^1a$ represents a group of the following formula:

Between lines 10 and 15, insert the following:

Table 1, for Compound No. 18, replace "1-MeHxCOCH$_2$" with -- 1-MeHx$^c$CO$_2$CH$_2$ --.
Table 1, for Compound No. 27, replace "Bu$^c$OCO$_2$CH$_2$" with -- Bu$^t$OCO$_2$CH$_2$ --.
Table 1, for Compound No. 33, replace "Pr$^i$OCO$_2$CH$_2$" with -- Pr$^i$CO$_2$CH$_2$ --.
Table 1, for Compound No. 47, replace "Bu$^t$CO$_2$CH$_2$" with -- Bu$^t$OCO$_2$CH$_2$ --
Table 1, for Compound No. 48, replace "Bu$^t$CO$_2$CHMe" with -- Bu$^t$OCO$_2$CHMe --

Column 10,
Line 47, replace " (Ic) " with -- (IIc) --.
Line 52, replace "preferrred" with -- preferred --.

Column 12,
Line 3, replace "paraoxybenzoates" with -- parahydroxybenzoates --.
Line 28, replace "anti-ulcereratives" with -- anti-ulceratives --.

Column 13,
Table 2, for *helicobacter pylori* strain 9470, for Compound No. 2, replace "$\leq 0.0006$" with -- $\leq 0.006$ --,

UNITED STATES PATENT AND TRADEMARK OFFICE
CERTIFICATE OF CORRECTION

PATENT NO.    : 6,180,621 B1
DATED         : January 30, 2001
INVENTOR(S)   : Isao Kawamoto et al.

It is certified that error appears in the above-identified patent and that said Letters Patent is hereby corrected as shown below:

Column 14,
Line 30, replace with 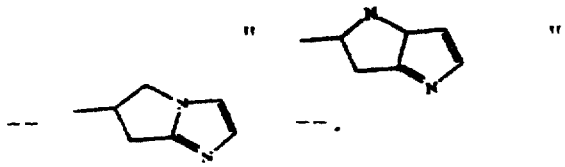

Line 59, replace "2-oxo4-pyrolidinyl" with -- 2-oxo-4-pyrroldinyl --.
Line 61, replace "2-oxo-4-pyrolidinyl" with -- 2-oxo-4-pyrroldinyl --.
Line 64, replace "2-oxo-4-pyrolidinyl" with -- 2-oxo-4-pyrroldinyl --.

Column 15,
Line 35, replace "ester" with -- esters --.
Line 52, replace "5-methyl-2-oxo-1,3-dioxolen4-ylmethyl" with -- 5-methyl-2-oxo-1,3-dioxolen-4-ylmethyl --.

Column 16,
Line 3, replace "2-(2-oxo4-pyrrolidinylthio)-6-(1-" with -- 2-(2-oxo-4-pyrrolidinylthio)-6-(1- --.
Line 10, replace "2-(1-methyl-2-oxo4-pyrrolidinylthio)-6-1-" with -- 2-(1-methyl-2-oxo-4-pyrrolidinylthio)-6-1- --.

Signed and Sealed this

Seventh Day of May, 2002

*Attest:*

*Attesting Officer*

JAMES E. ROGAN
*Director of the United States Patent and Trademark Office*